(12) United States Patent
Miller et al.

(10) Patent No.: US 8,092,878 B2
(45) Date of Patent: Jan. 10, 2012

(54) CRYOGENIC, ELASTOMERIC CLOSURE FOR CRYOGEN CONTAINERS

(75) Inventors: Timothy M. Miller, Limerick, PA (US); John N. Drummond, Phoenixville, PA (US); Douglas R. Duriez, Morgantown, PA (US)

(73) Assignee: West Pharmaceutical Services, Inc., Lionville, PA (US)

( * ) Notice: Subject to any disclaimer, the term of this patent is extended or adjusted under 35 U.S.C. 154(b) by 973 days.

(21) Appl. No.: 11/787,467

(22) Filed: Apr. 17, 2007

(65) Prior Publication Data

US 2007/0246468 A1 Oct. 25, 2007

Related U.S. Application Data

(60) Provisional application No. 60/744,972, filed on Apr. 17, 2006.

(51) Int. Cl.
*B29D 22/00* (2006.01)
*B65D 39/00* (2006.01)

(52) U.S. Cl. ...... 428/36.8; 428/35.7; 215/247; 215/355; 215/296

(58) Field of Classification Search ............. 428/35.7, 428/36.8; 215/247, 355, 296
See application file for complete search history.

(56) References Cited

U.S. PATENT DOCUMENTS

| | | | | |
|---|---|---|---|---|
| 3,531,444 A | * | 9/1970 | Behrens | 525/348 |
| 3,716,163 A | * | 2/1973 | Marcel | 215/320 |
| 4,138,183 A | | 2/1979 | Soos | |
| 4,404,819 A | | 9/1983 | Leonard | |
| 4,582,207 A | * | 4/1986 | Howard et al. | 215/247 |
| 5,374,689 A | * | 12/1994 | Rostek et al. | 525/332.7 |
| 5,947,274 A | * | 9/1999 | Taskis et al. | 206/204 |

FOREIGN PATENT DOCUMENTS

| | | | |
|---|---|---|---|
| GB | 2407314 A | | 4/2005 |
| JP | 89004454 B | * | 1/1989 |
| JP | 2004180859 A | | 7/2004 |
| JP | 2004231216 A | * | 8/2004 |
| WO | 02090821 A2 | | 11/2002 |

OTHER PUBLICATIONS

Machine Translation of JP2004231216A; 2004.*
English Abstract of JP89004454B; 1989.*
Supplementary European Search Report for the related European Application No. 07760769.5 dated Apr. 6, 2010.

* cited by examiner

*Primary Examiner* — Rena Dye
*Assistant Examiner* — James Yager
(74) *Attorney, Agent, or Firm* — Panitch Schwarze Belisario & Nadel LLP

(57) ABSTRACT

A multi-material, cryogenic, elastomeric closure is provided for sealing a container for samples of cryophilic biological materials, pharmaceuticals or the like. The closure includes at least one cryophilic elastomer having a glass transition temperature ($T_g$) below the cryogenic temperature to which the sample is to be subjected and at least one non-cryophilic elastomer having a $T_g$ above the cryogenic temperature. The cryophilic and non-cryophilic elastomers are present in such a manner as to maintain a complete seal of the container opening at the cryogenic temperature.

10 Claims, 1 Drawing Sheet

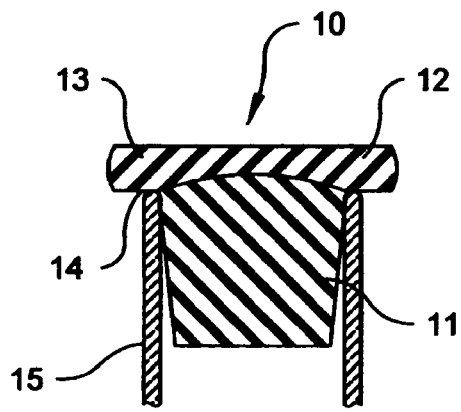
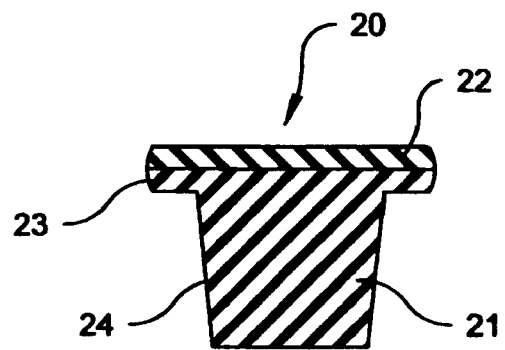
Fig. 1  Fig. 2
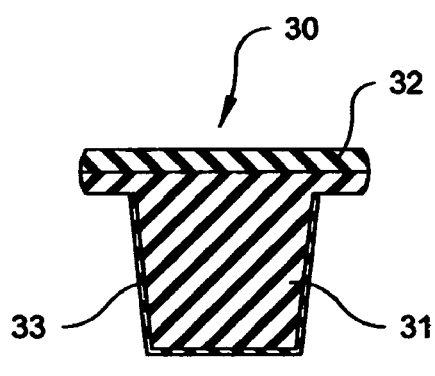
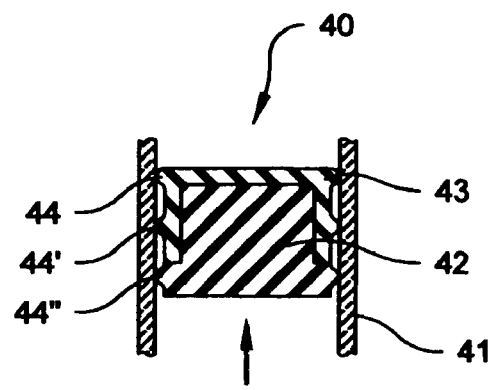
Fig. 3  Fig. 4

CRYOGENIC, ELASTOMERIC CLOSURE FOR CRYOGEN CONTAINERS

CROSS-REFERENCE TO RELATED APPLICATION

This application claims the benefit of U.S. provisional patent application 60/744,972, filed Apr. 17, 2006.

BACKGROUND OF THE INVENTION

The present invention is directed to cryogenic, elastomeric closures for cryogen containers. More particularly, the invention is directed to elastomeric stoppers for vials, plungers for syringes, and other closures for containers of materials, which must be processed or stored at cryogenic temperatures.

Stoppers and similar closures for vials and other containers for biological and pharmaceutical samples are typically made of elastomeric materials which provide a number of important functional properties, which are desirable for the closures. These include high resistance to permeation or migration of the material inside the container to the outside (escape of the contained material), as well as high resistance to permeation or migration of gases and liquids into the container from the outside (container/sample contamination), excellent sealing properties between the closure and the opening of the container to be closed, easy insertability or application of the closure to the container opening, and easy puncturability of the closure by a syringe needle or other instrument to insert or remove materials from the container.

Traditionally, stoppers and similar closures were made of natural rubber. Over the years, various synthetic rubbers and other elastomers have been developed to improve the permeation resistance, sealability and other desirable properties of the closures. These include, for example, butyl rubbers, isoprene rubbers, fluorocarbon polymers, etc. These elastomers have high permeation resistance, are easily puncturable by a syringe needle, and are sufficiently elastic to allow easy insertion into a container opening and to provide a good seal with the edge or wall of the opening. The containers are typically made of glass or plastic.

Many biological materials, pharmaceuticals and other cryophilic materials must be stored in sealed containers maintained at temperatures below about −80° C., for example to avoid deterioration or evaporation loss of these materials. The materials include, for example, blood, serum, proteins, peptides, stem cells, DNA, and other perishable biological liquids, on the one hand, and freeze-dried or lyophilized products, on the other hand. These materials are typically stored in stoppered glass vials or other glass or plastic containers with an elastomeric closure.

A problem with elastomeric closures for cryogenic applications is that currently available elastomeric closures undergo a glass transition between about −50° C. and −65° C. Once glass transition occurs, the elastomeric closure becomes hard, and even brittle, like glass, and the integrity of the seal between the closure and the container is compromised. This allows vapors, gases and possibly liquids to pass between the closure and the container opening, resulting in contamination of the contained sample and/or partial loss of the sample by evaporation or sublimation. While elastomeric materials are known which have a glass transition temperature ($T_g$) below about −80° C., such elastomeric materials are often expensive and/or may have undesirable properties, such as insufficient permeation resistance or tendencies to contaminate the contained product by chemicals present in the elastomer.

Accordingly, it would be desirable to have an elastomeric stopper or closure for vials and other containers, which are subjected to cryogenic temperatures for processing, storage and the like, such that the stopper or closure will maintain sufficient elastomeric properties to effect a complete seal of the container opening at temperatures below about −80° C., while retaining the desirable properties of permeation resistance, puncturability, and other functional or compatibility properties of current closures.

BRIEF SUMMARY OF THE INVENTION

According to the present invention, the above and other objects are achieved by a multi-material, cryogenic, elastomeric closure for cryophilic biological materials, pharmaceuticals, nutritional supplements, and other nutritional products. The multi-material closure comprises at least one cryophilic elastomer and at least one non-cryophilic elastomer, wherein the non-cryophilic elastomer has a glass transition temperature ($T_g$) above a cryogenic temperature to which the closure is to be subjected, and the cryophilic elastomer has a glass transition temperature ($T_g$) at or below the cryogenic temperature to which the closure is to be subjected.

The multi-material closure may have the cryophilic elastomer and non-cryophilic elastomer present in various forms. According to one embodiment of the invention, the closure may be a laminate of the cryophilic and non-cryophilic elastomers in which the two elastomers are physically and/or chemically bonded together, for example by compression molding.

According to another embodiment of the invention, the multi-material closure could comprise separate, cooperating components of the cryophilic elastomer and non-cryophilic elastomer. If desired, the non-cryophilic elastomer and the cryophilic elastomer could have shapes which positively interlock with each other to maintain the components in physical engagement.

It should be understood that the multi-material closures of the invention are not limited to a single cryophilic elastomer and a single non-cryophilic elastomer, nor are the closures limited to these types of elastomers alone. For example, the closures of the invention may also include other materials or components, such as barrier films, stopper covers and/or inserts, and the like.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a schematic, cross-sectional view of a two-material elastomeric stopper according to the invention, with the cryophilic elastomer on the top, inserted in an opening of a vial;

FIG. 2 is a schematic, cross-sectional view of a two-material elastomeric stopper similar to that of FIG. 1, but with the non-cryophilic elastomer on the top;

FIG. 3 is a schematic, cross-sectional view of a three-material stopper similar to that of FIG. 2, but with a barrier film around the cryophilic elastomer; and FIG. 4 is a schematic, cross-sectional view of a two-material elastomer plunger, with a cryophilic elastomer base and a non-cryophilic elastomer cap, inserted in a syringe barrel.

DETAILED DESCRIPTION OF THE INVENTION

As used herein, the term "closure" is intended to cover any device which seals an opening of a container in the manner of a plug, plunger or stopper, i.e., by having a resilient material press against the entire periphery of the opening to form a seal. Thus, according to the invention, the cryophilic elastomer is present in the closure in such a manner as to maintain a complete, continuous seal of an opening of the container by the closure at the cryogenic temperature.

As used herein, the term "container" is intended to cover any sealable receptacle or holder for a material which is subjected to cryogenic temperatures during processing, storage or the like. Containers may include, for example, vials, bottles, syringes, pre-filled drug delivery devices, laboratory vessels, and the like, which have an opening that must be sealed by a closure to maintain the integrity of the contents.

As used herein, "cryogenic temperature(s)" are considered to be temperatures of about −80° C. or below. These are the temperatures at which many biological materials, such as blood, serum, proteins, peptides, stem cells, DNA, and other perishable substances must be stored to maintain viability for long periods of time. Such storage includes dry ice storage (sublimation point −78.5° C.).

As used herein, "non-cryophilic elastomer" means an elastomer having a glass transition temperature ($T_g$) above cryogenic temperatures, i.e., above about −80° C. These elastomers include, but are not limited to natural rubbers, butyl rubbers, isoprene rubbers, fluorocarbon polymers, and other synthetic elastomeric polymers, and mixtures thereof. These non-cryophilic elastomers must have the usual elastomeric properties necessary for sealing containers containing perishable and/or volatile substances or materials, which are sensitive to oxygen, moisture and/or other environmental conditions, at temperatures above cryogenic temperatures. Such properties include high permeation resistance to liquids and gases, sufficient elasticity to be easily insertable within the container opening, yet to exert a pressure against the opening wall or edge for sealability, and puncturability to allow easy insertion of a syringe needle or the like, particularly when the container is brought back to room temperature.

As used herein, the term "cryophilic elastomer" means an elastomer having a $T_g$ at cryogenic temperatures, i.e., about −80° C. or below. Such elastomers include, for example, polybutadienes, silicones, fluorosilicones, nitrites, EPDM elastomers, and mixtures thereof. While it is not necessary that the cryophilic elastomer have the same degree of elasticity, high resistance to permeation and puncturability as the non-cryophilic elastomer, it is important that the cryophilic elastomer have excellent sealability with the wall or edge of the container opening at cryogenic temperatures, in order to provide a complete seal of the container opening under these low temperature conditions. That is, the cryophilic elastomer must substantially prevent the transmission of liquids and/or gases between the closure and the wall or edge of the container opening, in order to avoid contamination of the sample in the container by environmental gases or liquids or loss of the sample by evaporation or sublimation.

According to some embodiments of the invention, as illustrated for example in FIGS. 1-4, the multi-material cryogenic closure may be in the form of a laminate of the cryophilic elastomer with the non-cryophilic elastomer. Such a laminate may be formed, for example, by compression molding of layers or parts of the closure, which layers or parts individually comprise cryophilic elastomers and non-cryophilic elastomers. For this purpose, it is preferred to formulate the elastomers with similar cross-linking agents in order to obtain a cross-linked chemical bond between the layers or parts.

FIG. 1 shows an example of one possible embodiment of a laminated stopper in which a non-cryophilic elastomer forms the base 11 of the stopper 10, which is insertable into the open end of a vial 15 or other container opening. A cap 12 of cryophilic elastomer is laminated to the top of the base 11, so that annular flange 13 of the cap extends beyond the outer periphery of the base 11. In this manner, the underside 14 of the flange 13 of the cap 12 can provide a complete seal against the upper edge of the vial 15 or container opening.

FIG. 2 illustrates another embodiment of a laminated multi-material closure according to the invention. In this example, the stopper 20 comprises a base 21 of cryophilic elastomer and a cap 22 of non-cryophilic elastomer. The sidewall 24 and annular flange 23 provide a seal against the inner wall and upper edge, respectively, of the vial or container opening (not shown) when the stopper is inserted in the opening.

FIG. 3 shows an embodiment of a stopper similar to that of FIG. 2, but including a barrier layer around a portion of the cryophilic material base. Thus, stopper 30 includes a base 31 of cryophilic elastomer, a cap 32 of non-cryophilic elastomer, and a barrier film 33 coated or laminated around the bottom and sidewall of the base 31. The barrier film 33 may be, for example, a fluorinated polymer film which protects against contamination of the sample in the container by preventing the leaching of chemicals from the cryophilic elastomer into the container interior. Such barrier films 33 are advantageous when the cryophilic elastomer is a so-called "dirty elastomer." An example of such a barrier film is commercially available from West Pharmaceutical Services, Inc. under the trademark FluroTec®. Many fluorocarbon polymers actually have a high (about room temperature) $T_g$, but will retain a seal with the container opening at cryogenic temperatures, as long as a cryophilic elastomer is behind it as a support. That is, as long as the base material 31 remains elastic, the barrier film 33, which conforms to the periphery of the base, will maintain an adequate seal with the container opening.

FIG. 4 illustrates a closure in the form of a plug or plunger, which seals a syringe for dispensing pharmaceutical or biological materials or the like. In this embodiment the plunger 40 includes a base 42 which forms a core of cryophilic elastomer and a core cover 43 of non-cryophilic elastomer laminated to the base and contacting the material to be sealed in the syringe. The plunger 40 has annular ribs 44, 44', 44" located on its lateral periphery, which press against the inner wall of a barrel 41, to seal a material to be subjected to cryogenic temperature in the barrel 41 prior to and during travel of the plunger 40 in the distal direction of the barrel (indicated by the arrow). The plunger may be moved in the barrel by a piston rod (not shown) acting on the base 42 of cryophilic elastomer at its proximal end. It will be understood that the plunger need not have three annular ribs, but could have one, two or more, as desired. Thus, while the rib 44" on the cryophilic elastomer, which is in direct contact with the barrel wall at the proximal end of the plunger, ensures sealing at cryogenic temperatures, sealing at such temperatures can also be achieved by the ribs 44 and/or 44' of the base by virtue of the cryophilic elastomer core behind the ribs 44, 44' pressing against the inner surface of the non-cryophilic elastomer cover.

It is also possible to provide a physical bonding of the layers or parts if the elastomers are distinct, non-compatible materials. Thus, if it is desired to form the closure as a unitary two-component closure, the cryophilic elastomer and the non-cryophilic elastomer components may have shapes which interlock, for example a mushroom shaped projection of one part into a complementary recess in the other part, in order to hold the two components together without chemical or physical bonding. Further, it will be understood that the closures are not limited to the usual generally circular transverse cross-sections, but many have any desired size and shape to match those of the container opening.

The cryogenic closures described above may be manufactured in a number of different ways, depending upon the particular structure and materials of the closure. Examples of suitable methods may include separate molding and subsequent lamination of the two or more parts, co-molding of the parts after laying both materials in a mold, co-molding of the parts with a film laid on one or both materials, multi-shot injection molding, and rotary compression molding.

In a preferred method for manufacture of a stopper of the type shown in FIG. 1, the plug part or base 11 is first molded from a non-cryophilic material, such as a typical halobutyl pharmaceutical grade formulation, such as 4023/50 gray available from West Pharmaceutical Services, Inc. of Lionville, Pa. The cryophilic elastomer, such as a polybutadiene-based resin formulation is then laminated to the halobutyl base to form a cap 12. Both cryophilic and non-cryophilic elastomer formulations are then cured with conventional sulfur based cure systems, which must be compatible, such that the two formulations bond together to form an essentially continuous article.

An advantage of the cryogenic closures described above is that lyophilization times for products contained in the cryogen containers may be shortened, because a better seal is obtained between the closure and container at lower temperatures. Thus, up to now, it has been necessary to warm the container and closure up to the point of sealing by the elastomeric closure, and only then may the sealed container be removed from the lyophilization chamber. With the better seals of the present closures at lower temperatures the warming step may be omitted, and the container sealed by the closure can be removed from the chamber essentially immediately after completion of the lyophilization process.

The particular form of the multi-material cryogenic closure will depend upon many factors, including the type of opening being closed, the material of the container opening, the sensitivity of the contained sample to oxygen, moisture or the like (and therefore, the degree of permeation resistance required), the cryogenic temperatures to which the closure is to be subjected, the contamination potential of the cryophilic elastomer, and other factors. One skilled in the art will be able to design an appropriate form of elastomeric cryogenic closure consistent with these factors in view of the above disclosure.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A container assembly comprising:
    a container; and
    a multi-material, elastomeric, cryogenic plug or plunger for the container, wherein the cryogenic plug or plunger includes:
        a base of cryophilic elastomer forming a core having at one end a first peripheral sealing surface engaging an inner wall of the container and a sidewall at a second end of the core,
        a cover of non-cryophilic elastomer molded over the second end of the core, the cover having at least one second peripheral sealing surface for sealingly engaging the inner wall of the container and wherein the second peripheral sealing surface is positioned between the inner wall of the container and the core,
        the non-cryophilic elastomer having a glass transition temperature (Tg) above about −80 degrees Celsius, and
        the cryophilic elastomer having a glass transition temperature (Tg) below about −80 degrees Celsius.

2. The container assembly according to claim 1, wherein the cover is laminated to the base.

3. The container assembly according to claim 1, wherein the cover is mechanically interlocked with the base.

4. The container assembly according to claim 1, wherein the cover is co-molded with the base.

5. The container assembly according to claim 1, further comprising a barrier film surrounding portions of at least one of the base and cover exposed to an interior of the container and a sample.

6. The container assembly according to claim 1, wherein the cryophilic elastomer is at least one selected from the group consisting of polybutadienes, silicones, fluorosilicones, nitrites, and EPDM elastomers.

7. The container assembly according to claim 1, wherein the non-cryophilic elastomer is at least one selected from the group consisting of natural rubbers, butyl rubbers, isoprene rubbers, and fluorocarbon polymers.

8. The container assembly according to claim 1, wherein the container contains a sample to be subjected to a cryogenic temperature comprising a cryophilic material selected from the group consisting of biological materials, pharmaceuticals, nutritional supplements, and other nutritional products.

9. The container assembly according to claim 1, wherein the first and second peripheral sealing surfaces comprise annular ribs.

10. The container assembly according to claim 1, wherein the non-cryophilic elastomer comprises a pharmaceutical-grade halobutyl-based polymer formulation cured with a sulphur-based cure system and the cryophilic elastomer comprises a polybutadiene-based polymer formulation cured with a sulphur-based cure system, such that the two elastomers, when molded together to form the closure, form two distinct layers forming an essentially continuous article.

* * * * *